United States Patent

Wang

[11] 4,066,951
[45] Jan. 3, 1978

[54] APPARATUS FOR CALIBRATING MOISTURE MEASURING INSTRUMENT

[76] Inventor: Robert O. Wang, 2744 S. 61st St., Milwaukee, Wis. 53219

[21] Appl. No.: 729,128

[22] Filed: Oct. 4, 1976

[51] Int. Cl.² .......................................... G01R 27/26
[52] U.S. Cl. .................................... 324/61 R; 324/74
[58] Field of Search ....................... 324/61 R, 74, 130

[56] References Cited

U.S. PATENT DOCUMENTS 2,540,658   2/1951   DeGiers et al. ............... 324/61 R X

*Primary Examiner*—Stanley T. Krawczewicz
*Attorney, Agent, or Firm*—James E. Nilles

[57] ABSTRACT

Apparatus is disclosed for calibrating a known type of electrical instrument which is used for measuring the amount of moisture in a sample of grain or other particulate material. The instrument operates on the principle that the intensity of an electrostatic field will change in proportion to the moisture content of a material sample of predetermined size placed in the field, i.e., in proportion to the dielectric constant of the sample. The instrument comprises a test cell for receiving the sample and comprises a container having a concentrically disposed electrode therewithin which are part of a resonant electrical circuit; means for establishing a balanced electrostatic field of known intensity in the space between the container wall and electrode; means for measuring the change in field intensity (i.e., an increase in capacitance) effected by the moisture content of the sample and for providing a visual meter readout in the form of a numeric value correlated to the change in field intensity (and thus moisture content); and means for readjusting or recalibrating the instrument to re-establish the desired field intensity in the event of an undesired change therein. The calibration apparatus comprises a dielectric member for slideable insertion between the container wall and the electrode to a predetermined distance to effect a change in field intensity, means for holding the dielectric member in a desired position in the test cell, a pointer detachably connectable to the test cell, and a graduated scale on the dielectric member for cooperation with the pointer to indicate visually a numeric value which corresponds to a numeric value which will appear as the visual meter readout if the instrument is calibrated correctly.

22 Claims, 5 Drawing Figures

APPARATUS FOR CALIBRATING MOISTURE MEASURING INSTRUMENT

BACKGROUND OF THE INVENTION

1. Field of Use

This invention relates generally to apparatus for determining the accuracy of the calibration of a known type of electrical instrument which is used for measuring the moisture content of a sample of grain or other particulate material and to thereby enable recalibration of the instrument if an error exists.

2. Description of the Prior Art

U.S. Pat. No. 2,693,575 issued Nov. 2, 1954 to Greenwood et al for "Moisture Determining Device For Materials" discloses an electrical instrument which is used for measuring the amount of moisture in a sample of grain or other particulate material. This instrument generally comprises a test cell for holding a material sample of known type and size whose moisture content is to be determined and further comprises a comparative capacitance unit. The test cell comprises a cylindrical metal container open at its upper end and closed at its bottom end by an insulating disc and a cylindrical metal central electrode (insulated on the outside by a plastic sleeve) concentrically mounted within the container on the insulating disc in spaced relationship with the container. The test cell is, in effect, a capacitor and the container and the central electrode serve as the electrodes which are part of a resonant electrical circuit of the comparative capacitance unit. In operation, the resonant circuit is first balanced with the test cell empty. The material sample is then added to the cell, thus increasing its capacitance and the circuit is then rebalanced by means of a calibrated standard condenser and the change in capacity as indicated by this condenser, and a suitable indicator, is then correlated to the moisture content. In practice, moisture determining devices of this character are accurately calibrated during manufacture but are subject to miscalibration during use as the sensitive electrical components therein age or deteriorate during use. Accordingly, a means in the form of a manually adjustable trimmer condenser is provided to enable the instrument to be accurately recalibrated periodically. However, such recalibration requires the use of a controlled grain sample which takes the form of a measured amount of grain or other material having known dielectric characteristics and moisture content. Such samples are available in sealed containers from the U.S. government through specified channels of distribution which exist in the trade, and recalibration using such samples is carried out on a periodic basis. While this method of recalibrating moisture meters is very accurate and reliable, the procedures for obtaining the controlled samples are cumbersome and no calibration was heretofore possible unless the controlled sample was available.

SUMMARY OF THE INVENTION

In accordance with the present invention, there is provided apparatus for calibrating a known type of electrical instrument which is used for measuring the amount of moisture in a sample of grain or other particulate material. The instrument operates on the principle that the intensity of an electrostatic field will change in proportion to the moisture content of a material sample of predetermined size placed in the field, i.e., in proportion to the dielectric constant of the sample. The instrument comprises a test cell for receiving the sample and comprises a container having a concentrically disposed electrode therewithin which are part of a resonant electrical circuit; means for establishing a balanced electrostatic field of known intensity in the space between the container wall and electrode; means for measuring the change in field intensity (i.e., an increase in capacitance) effected by the moisture content of the sample and for providing a visual meter readout in the form of a numeric value correlated to the change in field intensity (and thus moisture content); and means for readjusting or recalibrating the instrument to re-establish the desired field intensity in the event of an undesired change therein. The calibration apparatus comprises a dielectric member for slideable insertion between the container wall and the electrode to a predetermined distance to effect a change in field intensity, means for holding the dielectric member in a desired position in the test cell, a pointer detachably connectable to the test cell, and a graduated scale on the dielectric member for cooperation with the pointer to indicate visually a numeric value which corresponds to a numeric value which will appear as the visual meter readout if the instrument is calibrated correctly.

Calibration apparatus in accordance with the present invention offers several advantages over the prior art. For example, it enables regular and frequent recalibration of all types of existing moisture meters which employ the electrostatic field principle. It eliminates the need to obtain controlled samples of grain or other particulate materials heretofore necessary for recalibration purposes thereby reducing the expense and trouble of obtaining the controlled sample and also enables the moisture meter to be recalibrated on a more frequent basis. Calibration apparatus in accordance with the present invention is relatively economical to manufacture and is simple and reliable in use. Other objects and advantages of the invention will hereinafter appear.

DESCRIPTION OF A PREFERRED EMBODIMENT

Figure 1:
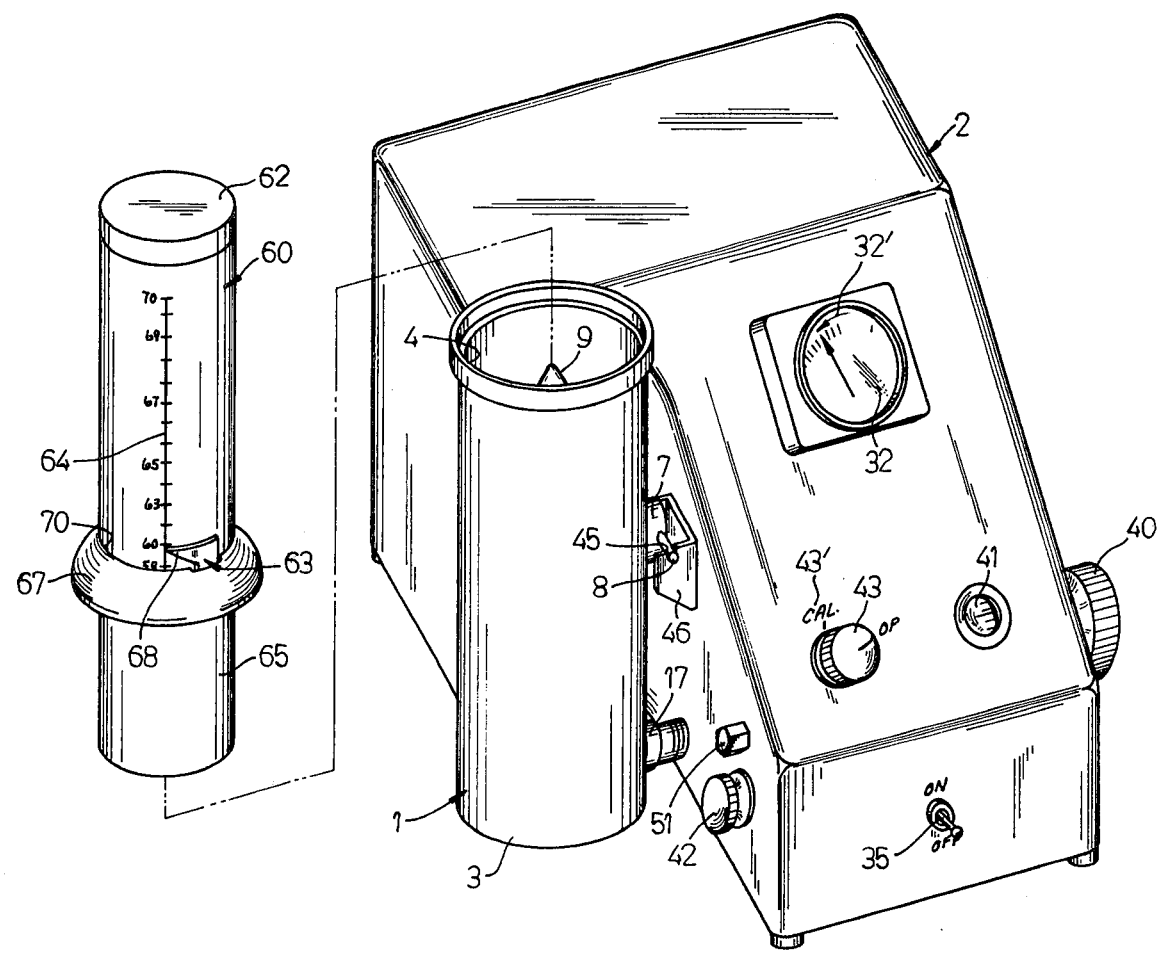
FIG. 1 is a perspective view of a moisture measuring instrument, its associated test cell, and calibration apparatus therefor in accordance with the invention.
Figure 2:
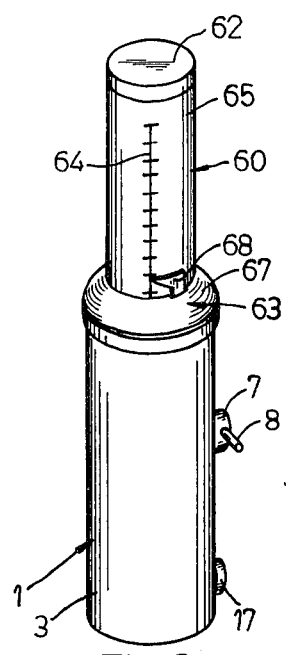
FIG. 2 is a perspective view of the test cell shown in FIG. 1 and showing it in association with calibration apparatus in accordance with the invention.

Referring to FIG. 1 of the drawing, there is shown a moisture measuring instrument comprising a test cell and a cooperative capacitance unit 2 for use therewith. FIGS. 1, 2, 3, and 4 show apparatus in accordance with the invention for calibrating the moisture measuring instrument, which apparatus is hereinafter described in detail.

Figure 3:
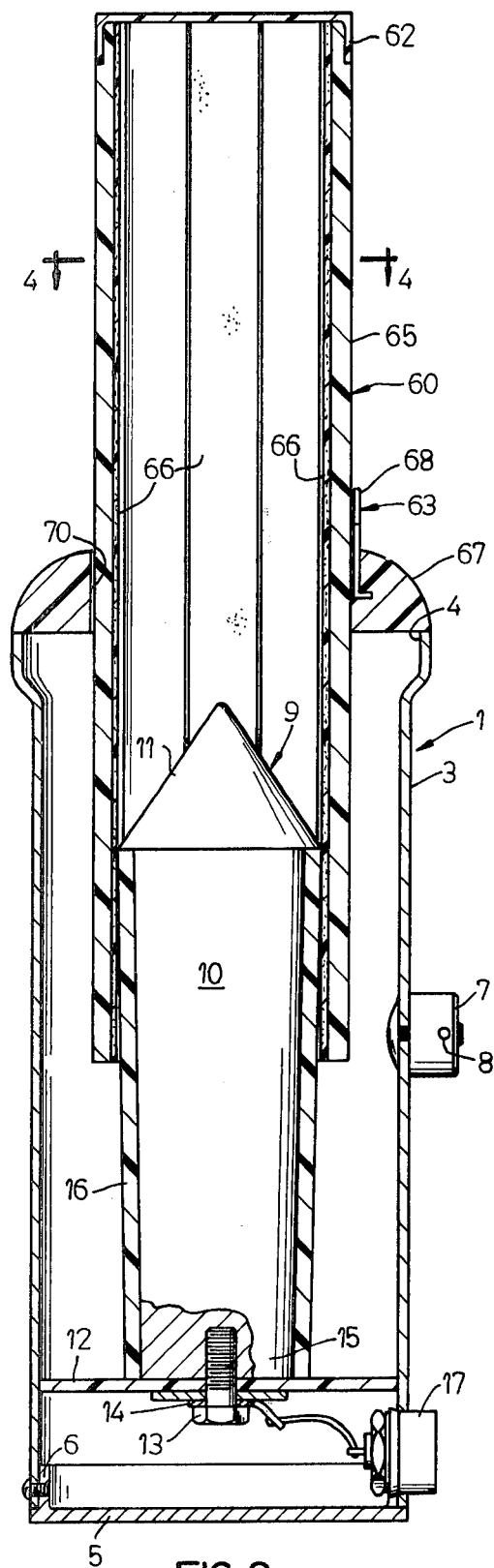
FIG. 3 is an enlarged cross-sectional view of the test cell and calibration apparatus shown in FIG. 2.

Reference to FIG. 3 of the accompanying drawings will show the details of construction of the test cell 1 and it will be seen that it consists of a cylindrical container 3 being open at the upper end 4 thereof and closed by means of a base plate 5 which is detachably secured to the base of the cylinder by screws or the like passing through the wall of the cylinder and an upstanding annular shoulder 6 formed upon the base plate 5.

The aforementioned outer container 3 constitutes one of the electrodes of this test cell and is connected to the unit 2 by means of a hanger 7 extending from the side of the cylinder 3, said hanger including a pair of outstanding prongs 8 which engage the unit in a manner hereinafter to be described.

The central electrode 9 of the test cell comprises an inverted truncated conical portion 10 surmounted by a material dispersal cap 11 which ensures that material poured into the cell is distributed evenly around the central electrode.

This electrode is secured concentrically within the cylindrical container 3 upon an insulating disc 12 spanning the container in spaced relationship above the end cap 5. A bolt 13 passes through a connector 14, through the disc 12, and is screw-threadably engagable within the base 15 of the central electrode 9 thus maintaining the central electrode in equal spaced relationship to the walls of the cylinder 3. A plastic sleeve 16 surrounds the central electrode and prevents the possibility of a direct connection between electrodes should the material being tested act as a high resistance conductor. Furthermore, due to the concentration of field at the central electrode in such a concentric arrangement, the sleeve serves to prevent small portions of the sample, which might differ from the main body of the sample, from having a disproportionate effect on the whole.

Means are provided to eliminate the increased effective dielectric constant of the material when loaded into the cell which is caused if the material packs and becomes more dense at the lower ends thereof. In this embodiment, this has been minimized by forming the main portion 10 of the central electrode in the inverted truncated cone as hereinbefore described, thereby giving an increased distance between the central electrode and the walls of the outer container at the base thereof, this distance gradually decreasing towards the upper ends of the two electrodes.

The aforementioned connector 14 extends from the base of the central electrode to a coaxial terminal 17 also provided on the wall of the outer container 3 immediately below the aforementioned hanger 7 and this, together with the hanger 7 enables the test cell 1 to be connected and disconnected from the unit 2 as desired. The coaxial terminal connects the cell electrically to the unit 2.

Figure 5:
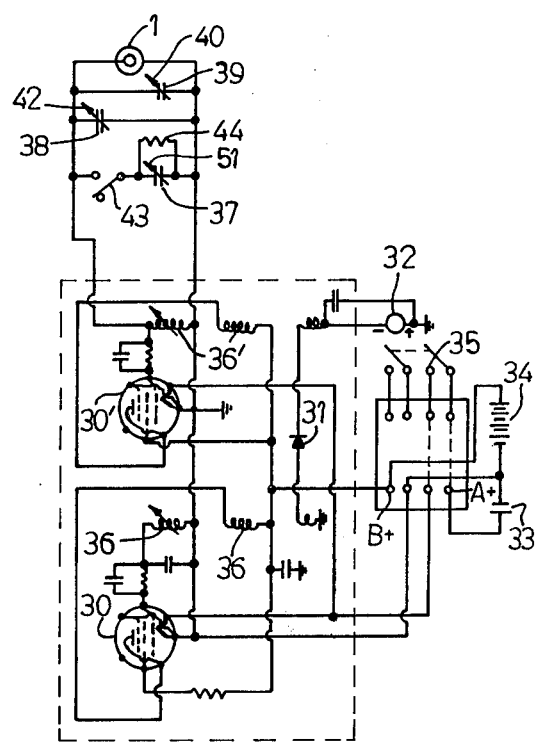
FIG. 5 is a schematic diagram of the electrical circuit of the moisture measuring instrument shown in FIG. 1.

The electronic unit 2 associated with the test cell 1 takes the form of a comparative capacitance unit the schematic wiring diagram of which is shown in detail in FIG. 5. The circuit comprises a pair of oscillators 30 and 30' linked by a coupling circuit which include a germanium diode 31 and a milliammeter 32. Power is supplied to the circuit by means of the two batteries 33 and 34, the former supplying the A+ current to the filaments and the latter, the B+ current as indicated, a multiple switch 35 being provided to switch the circuit on and off as required.

The resonant circuit of the oscillator 30 includes an inductance 36 and the frequency of this oscillator is fixed. The resonant circuit of the other oscillator 30' includes an inductance 36' and four capacitances, condensers 37, 38, and 39, and the cell 1 which is shown schematically in the wiring diagram of FIG. 5. Condenser 39 is calibrated variable standard condenser operated by knob 40 in FIG. 1, the calibration showing by means of the dial 41 on the face of the instrument. Condenser 38 is the trimming condenser and is operated by knob 42 on the opposite side of the instrument to knob 40. Condenser 37 is a fixed standard condenser having an associated switch 43 and a resistor 44 in circuit therewith of such a value as to make the condenser 37 the equivalent in both dielectric constant and loss factor to a standard sample of grain having a given moisture content placed in the cell. In this example, the sample has been arbitrarily set at 150 grams having 15% moisture, the grain being wheat.

A recalibration capacitor 37 which is manually adjustable by means of a knob 51 shown, when required, uses the calibration apparatus in accordance with the invention as hereinafter described.

Proceeding now to describe the operation, the empty cell 1 is first connected to the side of the unit 2 by means of the hanger 7 and coaxial terminal 17, it being understood that the latter connects the cell electronically to the resonant circuit of the oscillator 30' as signified in FIG. 5. The aforementioned prongs 8 of the hanger 7 engage within slots 45 provided in offstanding lugs 46 situated at the left-hand side of the instrument as shown in FIG. 1.

The main switch 35 is then moved to the "on" position thus connecting the batteries 33 and 34 to the circuit. In this connection, although batteries have been shown as a source of power in this embodiment, it will be appreciated that, if desired, a power pack may be supplied so that the unit may be connected to the main source of electrical supply normally present in most places where the device is to be used.

The switch 43 is then closed thus bringing into the circuit the calibrating condenser 37 and its resistor 44 and, in this connection, in FIG. 1, this position is indicated by the letters "CAL" and numbered 43'. The calibrated variable condenser 39 is then turned until a predetermined dial reading shows under the hair-line at 41, this position being a calibrating position and being marked on the dial of this condenser. Trimming condenser 38 is now adjusted by means of knob 42 until there is a minimum flow of current in the coupling circuit between oscillators 30 and 30', this minimum flow being shown on the meter 32. For convenience, an arrow 32' is provided on the dial of the meter with the head directed towards the left thereof with relation to FIG. 1, this arrow indicating the direction that the needle of the meter should move in order to indicate the minimum current flow.

When this minimum flow is obtained, the instrument is calibrated ready for use and the switch 43 is open thus taking the standard condenser 37 out of the circuit. In this connection, the letters "OP" are shown on the face of the instrument and represents "operate" as contrasted to "calibrate."

A sample of the grain or material to be tested is then carefully weighed as specified on charts supplied with the instrument, which has been calibrated in the range from 40° F. to 104° F. It is important that the temperature of the sample be ascertained prior to the tests being taken and this can be done by any standard method. This weighed sample is now placed within the test cell 1. It will be seen that the sample of the material now loaded within the test cell effects the circuit capacity of the oscillator 30' thus detuning same causing a current to flow in the coupling circuit. Therefore, power will be transferred from one oscillator to another in an effort to keep the two locked in frequency and, in this connection, it should be noted that a change in the circuit capacity of oscillator 30' of as little as 0.01 mmf will cause a change in the circulating current as indicated by the meter. In order to bring the tuning of the oscillator 30' into alignment with that of oscillator 30, the variable calibrated condenser 39 is rotated by means of knob 40 until once again there is a minimum current flow within the coupling circuit as indicated by the meter 32. In other words, the needle of this meter should be as far to the left of the dial as possible (with reference to FIG. 1). The reading of the calibrated condenser is then compared to a chart prepared for the material being tested whereupon the percentage moisture can be read from the chart. In this connection, it will be appreciated that charts are provided for any material being tested, these charts being prepared by the correlation of many determinations of moisture by laboratory methods.

Means are provided to check the over-all accuracy of the instrument at any time thus enabling the operator to ensure that the readings taken are accurate determinations of the moisture present in the material being tested. This procedure entails calibrating the instrument as hereinabove described and then employing the calibration apparatus in accordance with the invention to determine if the instrument is in proper adjustment and, if not, to then enable desired recalibration by means of the knob 51 to readjust recalibration capacitor 37.

As FIGS. 1, 2, 3, and 4 show, the calibration apparatus comprises a dielectric member 60 for slideable insertion between the wall of container 3 and the electrode 9 to a predetermined distance to effect a change in field intensity, means hereinafter described for holding the dielectric member 60 in a desired position in the test cell 1, a pointer assembly 63 detachably connectable to the test cell, and a graduated scale 64 on the dielectric member 60 for cooperation with the pointer assembly 63 to indicate visually a numeric value which corresponds to a numeric value which will appear as the visual meter readout on scale 41 if the instrument is calibrated correctly.

More specifically, dielectric member 60 takes the form of a hollow open-ended cylinder 65 fabricated of dielectric material such as PVC plastic or the like. The upper end of cylinder 65 is closed by a glued-in place end cap 62, also of plastic.

Figure 4:
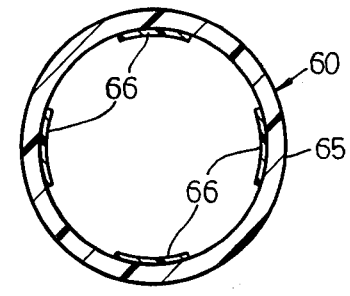
FIG. 4 is a cross-sectional view of a component of the calibration apparatus taken on line 4—4 of FIG. 3.

The cylinder 65 is adapted to be slid over central electrode 9 in test cell 1 into the space between the electrode 9 and container 3. Cylinder 65 is frictionally maintained in desired axial positions in the electrostatic field by means of felt-like strips of dielectric material 66 which FIGS. 3 and 4 show are glued inside the cylinder.

The removable pointer assembly 63, which cooperates with the graduated scale 64 on dielectric member 60 to indicate the extent to which the dielectric member is inserted in the field (and thus the extent to which the capacitance of test cell 1 is increased), comprises a support ring 67, formed of dielectric material such as plastic, which is adapted to rest on and firmly engage the mouth or upper end 4 of container 3 in fixed relationship when placed thereon. Support ring 67 affords support for a pointer 68, fabricated of a sheet metal stamping for example, and secured to ring 67 as by gluing. Pointer assembly 63 always assumes the same relative position on container 3 when placed thereon. Support ring 67 is provided with a central opening 70 to slideably accommodate passage of cylinder 65 as the latter is moved or slid to various desired test positions.

A graduated scale 64 is imprinted or otherwise attached to the outer surface of cylinder 65 and is graduated in numerals (shown as ranging from numerals 59 to 70) which correspond to similar numerals on a portion of the scale 41 on the instrument 2. The range of numerals selected for scale 64 are related to meter readings which would most likely appear on scale 41 if a particular sample of material were being tested for moisture content. For example, for testing Eastern Barley, sample size 225 grams, requiring an initial calibration setting of 53, the graduated scale 64 would range between 59 to 70. For other types of grain or particulate materials, the scale to be provided would be determined from the aforementioned charts which exist for particular materials to be tested.

The spacing between graduation on scale 64 is initially arrived at on a pragmatic basis. That is to say, the scale 64 (in a desired range) is laid out by employing a moisture measuring instrument which is known to be in substantially perfect adjustment and calibration, and a graduation mark is applied at each point when the meter 41 shows the appropriate readout as the cylinder 65 is moved to various positions in the electrostatic field. Once a model dielectric member 65 and model scale 64 are fabricated, any desired number of duplicate devices can be fabricated for use and sale.

The calibration apparatus is employed as follows. First, the instrument is to be calibrated as hereinbefore described, as if to put it in readiness to test a particular sample of material. Use is made of the hereinbefore mentioned charts for this purpose. However, instead of using a controlled sample of material, the calibration apparatus in accordance with the invention is employed instead.

The support ring 67 is put in place, the dielectric member 60 is inserted so that scale 64 therein is opposite pointer 68 at some desired point, such as a calibration point specified on the hereinbefore mentioned chart. As will be understood, the dielectric member 60 used will be one which is precalibrated or designed for a particular type of material. The calibrated variable condenser 39 is then turned until a predetermined dial reading shows under the hair-line at 41, this position being a calibrating position and being marked on the dial of this condenser. Trimming condenser 38 is now adjusted by means of knob 42 until there is a minimum flow of current in the coupling circuit between oscillators 30 and 30', this minimum flow being shown on the meter 32. When this minimum flow is obtained, the instrument is calibrated ready for use provided, of course, that the numeral on scale 64 designated by pointer 68 corresponds to the scale reading under hair-line 41. If such correspondence occurs, the instrument is properly calibrated. However, instead of merely relying on one reading, the dielectric member 60 can be moved to various positions to ensure accuracy. If, however, there is not correspondence between the dial reading at hair-line 41 and the number on scale 64 designated by pointer 68, this indicates that the instrument is out of calibration, and such misregistration is corrected by moving knob 51 to effect the necessary adjustment of recalibration capacitor 37 in the conventional manner.

In practice, the user of the instrument does not normally attempt to recalibrate the instrument as this is preferably done at the factory because in many instances, other internal adjustments to the instrument need to be made. However, the user of the instrument employs apparatus in accordance with the invention to check the accuracy of his instrument usually at the commencement of each days work or for each cargo of grain to be tested.

It is to be understood that although capacitor 37 is shown herein as the capacitor whereby the instrument is recalibrated, other types of instruments having other components requiring adjustment for purposes of recalibration are intended to be within the scope of the present invention.

Similarly, although the means for maintaining the dielectric member 60 inserted in a predetermined position between the electrodes is shown as comprising felt-like strips of dielectric material 66, other suitable components could be employed.

Also, although a pointer 68 is shown for association with the graduated scale 64, other types of indicators, such as a wire or hair-line or the like could be employed for the sake of greater accuracy.

In the embodiment shown, only a single scale 64 is shown on member 62. However, it will be understood that other scales similar to scale 64, but covering a different numerical range could be applied to a single common cylinder thereby further enhancing the utility of the invention and reducing the number of cylinders a user would need to keep on hand.

I claim:

1. In combination:
  an instrument for measuring the moisture content of a sample of material;
  said instrument comprising a test cell including a pair of spaced apart electrodes, one of said electrodes having the form of a hollow container open at one end and the other of said electrodes being disposed within said container, a meter providing a readout indicative of said moisture content, and adjustable means selectively operable for recalibrating said instrument to ensure that said meter provides a correct readout;
  and apparatus for indicating whether or not said instrument is properly calibrated so that said adjustable means may be selectively operated to effect recalibration, if necessary, said apparatus comprising:
  a removable member for insertion between the electrodes of said test cell;
  means between said member and at least one of said electrodes for frictionally maintaining said member inserted in a predetermined position between said electrodes;
  a pointer having a predetermined position with respect to said test cell; and
  scale means on said member for cooperation with said pointer to indicate the extent to which said member is inserted between said electrodes and providing a readout on said scale correlated to the readout of the meter of said instrument when said instrument is properly calibrated and facilitating adjustment of said adjustable means to effect recalibration if said readout on said scale does not correlate to said readout of said meter.

2. A combination according to claim 1 wherein said means for maintaining said member inserted in a predetermined position comprises an electrically insulating element secured to said means for effecting frictional engagement between said removable member and at least one of said electrodes.

3. A combination according to claim 1 including means for detachably mounting said pointer in a predetermined position with respect to said test cell.

4. A combination according to claim 2 wherein said means for effecting frictional engagement comprises at least one electrically insulated member secured to said removable member.

5. A combination according to claim 3 wherein said means for detachably mounting said pointer comprises an electrically insulated ring for detachably mounting on said test cell, said ring having an opening therethrough for accommodating passage of said member.

6. In combination:
  an instrument for measuring the moisture content of a sample of material;
  said instrument comprising a test cell including a pair of spaced apart electrodes, one of said electrodes having the form of a hollow cylindrical container open at one end and the other of said electrodes having the form of a centrally disposed electrode concentrically mounted within said container, a meter providing a readout indicative of said moisture content, and adjustable means selectively operable for recalibrating said instrument to ensure that said meter provides a correct readout;
  and apparatus for indicating whether or not said instrument is properly calibrated so that said adjustable means may be selectively operated to effect recalibration, if necessary, said apparatus comprising:
  a hollow cylindrical member for insertion between the electrodes of said test cell;
  means for maintaining said member inserted in a predetermined position between said electrodes;
  a pointer having a predetermined position with respect to said test cell; and
  scale means on said member for cooperation with said pointer to indicate the extent to which said member is inserted between said electrodes and providing a readout on said scale correlated to the readout of the meter of said instrument when said instrument is properly calibrated and facilitating adjustment of said adjustable means to effect recalibration if said readout on said scale does not correlate to said readout of said meter.

7. A combination according to claim 6 wherein said means for mounting said member inserted in a predetermined position comprises means for effecting frictional engagement between said hollow cylindrical member and at least one of said electrodes.

8. A combination according to claim 6 including means for detachably mounting said pointer in a predetermined position with respect to said test cell.

9. A combination according to claim 7 wherein said means for effecting frictional engagement comprises at least one electrically insulated member secured to the inside wall of said hollow cylindrical member.

10. A combination according to claim 8 wherein said means for detachably mounting said pointer comprises an electrically insulated ring for detachably mounting on said container, said ring having an opening therethrough for accommodating passage on said hollow cylindrical member.

11. In combination:
  an instrument for measuring the moisture content of a sample of material;
  said instrument comprising a test cell including a pair of spaced apart electrodes between which an electrostatic field is established, one of said electrodes having the form of a hollow cylindrical container open at one end and the other of said electrodes having the form of a centrally disposed electrode concentrically mounted within said container, a meter providing a readout indicative of said moisture content, and adjustable means selectively operable for recalibrating said instrument to ensure that said meter provides a correct readout;

and apparatus for indicating whether or not said instrument is properly calibrated so that said adjustable means may be selectively operated to effect recalibration, if necessary, said apparatus comprising:

a hollow cylindrical member for dielectric material for insertion into said electrostatic field between the electrodes of said test cell;

means for maintaining said member inserted in a predetermined position between said electrodes, said means comprising at least one electrically insulated member secured to the inside wall of said hollow cylindrical member for frictional engagement with said centrally disposed electrode;

a pointer;

pointer support means for detachably mounting said pointer in a predetermined position with respect to said test cell, said pointer support means comprising an electrically insulated ring for detachably mounting on said container, said ring having a central opening therethrough for accommodating passage of said hollow cylindrical member; and scale means on said member for cooperation with said pointer to indicate the extent to which said member is inserted between said electrodes and providing a readout on said scale correlated to the readout of the meter of said instrument when said instrument is properly calibrated and facilitating adjustment of said adjustable means to effect recalibration if said readout on said scale does not correlate to said readout of said meter.

12. In combination:

an instrument for measuring the moisture content of a sample of material;

said instrument comprising a test cell including a pair of spaced apart electrodes and a meter providing a readout indicative of said moisture content, one of said electrodes being a hollow container open at one end and the other of said electrodes being disposed within said container;

and apparatus for indicating whether or not said instrument is properly calibrated, said apparatus comprising:

a removable member for insertion between the electrodes of said test cell;

means between said member and at least one of said electrodes for frictionally maintaining said member inserted in a predetermined position between said electrodes;

a pointer having a predetermined position with respect to said test cell; and scale means on said member for cooperation with said pointer to indicate the extent to which said member is inserted between said electrodes and providing a readout on said scale correlated to the readout of the meter of said instrument when said instrument is properly calibrated.

13. A combination according to claim 12 wherein said means for maintaining said member inserted in a predetermined position comprises means for effecting frictional engagement between said removable member and at least one of said electrodes.

14. A combination according to claim 12 including means for detachably mounting said pointer in a predetermined position with respect to said test cell.

15. A combination according to claim 13 wherein said means for effecting frictional engagement comprises at least one electrically insulated member secured to said removable member.

16. A combination according to claim 14 wherein said means for detachably mounting said pointer comprises an electrically insulated ring for detachably mounting on said test cell, said ring having an opening therethrough for accommodating passage of said removable member.

17. In combination:

an instrument for measuring the moisture content of a sample of material;

said instrument comprising a test cell including a pair of spaced apart electrodes, one of said electrodes having the form of a hollow cylindrical container open at one end and the other of said electrodes having the form of a centrally disposed electrode concentrically mounted within said container, and a meter providing a readout indicative of said moisture content;

and apparatus for indicating whether or not said instrument is properly calibrated, said apparatus comprising:

a hollow cylindrical member for insertion between the electrodes of said test cell;

means for maintaining said member inserted in a predetermined position between said electrodes;

a pointer having a predetermined position with respect to said test cell; and scale means on said member for cooperation with said pointer to indicate the extent to which said member is inserted between said electrodes and providing a readout on said scale correlated to the readout of the meter of said instrument when said instrument is properly calibrated.

18. A combination according to claim 17 wherein said means for mounting said member inserted in a predetermined position comprises means for effecting frictional engagement between said hollow cylindrical member and at least one of said electrodes.

19. A combination according to claim 17 including means for detachably mounting said pointer in a predetermined position with respect to said test cell.

20. A combination according to claim 19 wherein said means for effecting frictional engagement comprises at least one electrically insulated member secured to the inside wall of said hollow cylindrical member.

21. A combination according to claim 19 wherein said means for detachably mounting said pointer comprises an electrically insulated ring for detachably mounting on said container, said ring having an opening therethrough for accommodating passage of said hollow cylindrical member.

22. In combination:

an instrument for measuring the moisture content of a sample of material;

said instrument comprising a test cell including a pair of spaced apart electrodes between which an electrostatic field is established, one of said electrodes having the form of a hollow cylindrical container open at one end and the other of said electrodes having the form of a centrally disposed electrode concentrically mounted within said container, and a meter providing a readout indicative of said moisture content;

and apparatus for indicating whether or not said instrument is properly calibrated, said apparatus comprising:

a hollow cylindrical member for dielectric material for insertion into said electrostatic field between the electrodes of said test cell;

means for maintaining said member inserted in a predetermined position between said electrodes, said means comprising at least one electriclly insulated member secured to the inside wall of said hollow cylindrical member for frictional engagement with said centrally disposed electrode;

a pointer;

pointer support means for detachably mounting said pointer in a predetermined position with respect to said test cell, said pointer support means comprising an electrically insulated ring for detachably mounting on said container, said ring having a central opening therethrough for accommodating passage of said hollow cylindrical member; and scale means on said member for cooperation with said pointer to indicate the extent to which said member is inserted between said electrodes and providing a readout on said scale correlated to the readout of the meter of said instrument when said instrument is properly calibrated.

* * * * *